United States Patent [19]

Mazzocco

[11] Patent Number: 5,776,191
[45] Date of Patent: Jul. 7, 1998

[54] FIXATION SYSTEM FOR INTRAOCULAR LENS STRUCTURES

[75] Inventor: Thomas R. Mazzocco, Granada Hills, Calif.

[73] Assignee: Staar Surgical Company, Monrovia, Calif.

[21] Appl. No.: 356,789

[22] Filed: Dec. 13, 1994

Related U.S. Application Data

[63] Continuation of Ser. No. 184,503, Jan. 19, 1994, abandoned, which is a continuation of Ser. No. 400,655, Jul. 22, 1982, abandoned, which is a continuation-in-part of Ser. No. 346,105, Feb. 5, 1982, Pat. No. 4,573,998.

[51] Int. Cl.$^6$ ...................................................... A61F 2/16
[52] U.S. Cl. ................................................................ 623/6
[58] Field of Search ............................................... 623/6

[56] References Cited

U.S. PATENT DOCUMENTS

| | | | |
|---|---|---|---|
| 3,991,426 | 11/1976 | Flom et al. | 623/6 |
| 3,992,563 | 11/1976 | Tanaka | 623/6 |
| 4,053,953 | 10/1977 | Flom et al. | 623/6 |
| 4,056,855 | 11/1977 | Kelmar | 623/6 |
| 4,080,709 | 3/1978 | Poler | 623/6 |
| 4,092,743 | 6/1978 | Kelmar | 623/6 |
| 4,110,848 | 9/1978 | Jensen | 623/6 |
| 4,118,808 | 10/1978 | Poler | 3/13 |
| 4,122,556 | 10/1978 | Poler | 623/6 |
| 4,153,641 | 5/1979 | Deichert et al. | 351/160 H X |
| 4,172,297 | 10/1979 | Schlegel | 623/6 |
| 4,203,168 | 5/1980 | Rainin et al. | 623/6 |
| 4,206,518 | 6/1980 | Jardon et al. | 623/6 |
| 4,214,585 | 7/1980 | Bailey, Jr. | 623/4 X |
| 4,244,060 | 1/1981 | Hoffer | 623/6 |
| 4,251,887 | 2/1981 | Anis | 3/13 |
| 4,253,199 | 3/1981 | Banto | 623/6 |
| 4,254,509 | 3/1981 | Tennant | 623/6 |
| 4,262,370 | 4/1981 | Hartstein | 623/6 |
| 4,315,337 | 2/1982 | Choyce | 3/13 A |
| 4,365,360 | 12/1982 | Ong | 3/13 A |
| 4,377,329 | 3/1983 | Poler | 3/13 |
| 4,402,579 | 9/1983 | Poler | 3/13 |
| 4,409,691 | 10/1983 | Levy | 3/13 |
| 4,463,457 | 8/1984 | Kelmon | 623/6 |

FOREIGN PATENT DOCUMENTS

| | | | |
|---|---|---|---|
| 1103399 | 5/1955 | France | 3/13 |
| 2717706 | 10/1978 | Germany | 623/6 |

OTHER PUBLICATIONS

"The Single Piece Perspex Posterior Chamber Lens" Mar. 1981.
"The Kratz Technique for Cataract Extraction w/Lens Implant" Mar. 1981.
"CILCO Lens Styles" Oct. 1982.
"The Sincoe Posterior Chamber Lens" Feb. 1980.

*Primary Examiner*—Mary Beth Jones
*Attorney, Agent, or Firm*—Frank Frisenda, Jr.

[57] ABSTRACT

The invention provides an improved system for atraumatic fixation of intraocular lens structures which comprises a deformable, compliant, peripheral frame and a concentrically disposed optical zone portion which, in one embodied form, is resiliently suspended from the frame by a plurality of compliant fibers or webbing. Accordingly, the invention facilitates surgical placement of the intraocular lens structure in the eye without the requirement of sutures, and without iris involvement, thereby providing a safer and more convenient surgical procedure. The unique fixation system may be utilized for placement of intraocular lenses having either a rigid or a deformable optical zone portion in the anterior chamber or posterior chamber of the eye following cataract removal procedures.

15 Claims, 3 Drawing Sheets

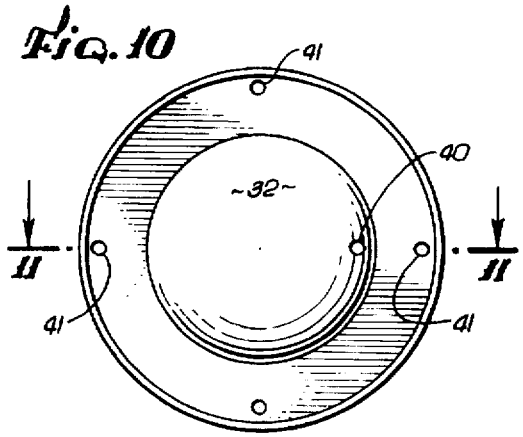
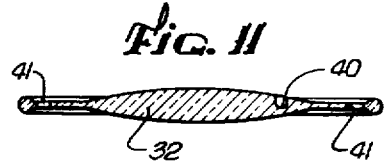
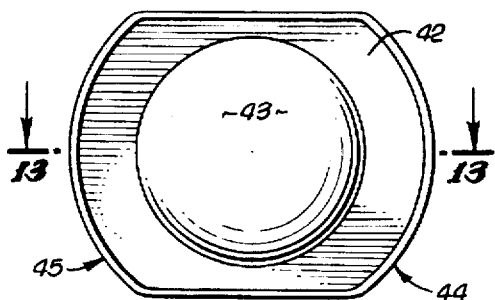
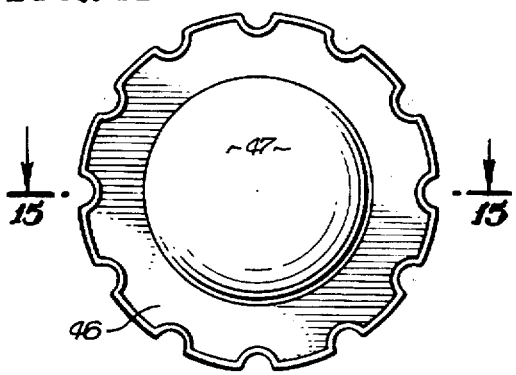
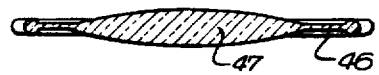
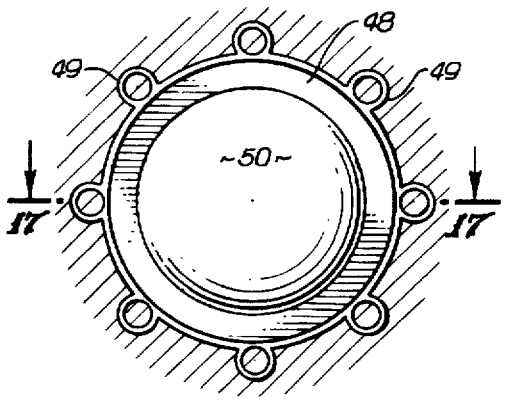
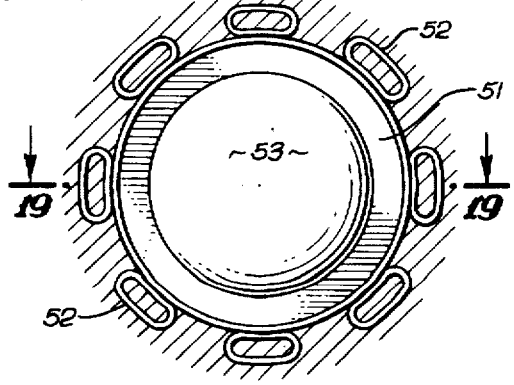
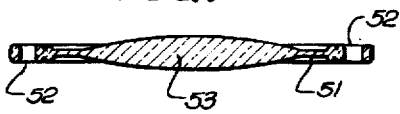

FIXATION SYSTEM FOR INTRAOCULAR LENS STRUCTURES

CROSS-REFERENCE TO RELATED APPLICATIONS

This application is a continuation of U.S. application Ser. No. 08/184,503 filed Jan. 19, 1994, now abandoned, which is a continuation of U.S. application Ser. No. 06/400,655 filed Jul. 22, 1982, now abandoned, which is a continuation-in-part of 06/346,105 filed Feb. 5, 1982, now U.S. Pat. No. 4,573,998.

BACKGROUND OF THE INVENTION

Intraocular lenses have gained wide acceptance in replacement of human crystalline lens after a variety of cataract removal procedures. The human crystalline lens is generally recognized to be a transparent structure having a thickness of about 5 millimeters and diameter of about 9 millimeters. The lens is suspended behind the iris by zonular fibers which connect the lens to the ciliary body. A lens capsule surrounds the lens, the front portion of the capsule being commonly known as the anterior capsule and the back portion commonly known as the posterior capsule.

Numerous procedures for the removal of cataracts have been developed in which the lens is removed from the eye and replaced by an artificial lens implant. The extraction procedure may be generally categorized as intracapsular (in which the lens is removed together with the lens capsule) or extracapsular (in which the anterior capsule is removed with the lens, and the posterior capsule is left intact).

Since Ridley implanted the first artificial lens in about 1949, the problems associated with cataract extraction and lens implantation have received a great deal of attention from ophthalmic surgeons.

Various types of artifical lenses have been proposed, and appropriate surgical procedures have been developed which strive to reduce patient discomfort and reduce post-operative complications. Reference is made in this connection to *Pseudophakos* by N. Jaffe, et al; "History of Intraocular Implants" by D. P. Choyce (Annals of Ophthalmology, October 1973); U.S. Pat. No. 4,251,887 issued to Anis on Feb. 24, 1981; U.S. Pat. No. 4,092,743 issued to Kelman on Nov. 8, 1977; "Comparison of Flexible Posterior Chamber Implants", presented at the American Intraocular Implant Society Symposium Apr. 23, 1982, by Charles Beckert, M.D.; and "The Simcoe Posterior Lens" (Cilco, Inc. 1980); which disclosures are hereby incorporated by this reference.

Of particular interest in the context of the present invention is the development of surgical techniques requiring relatively small incisions in the ocular tissue for the removal of cataracts as disclosed in U.S. Pat. No. 4,002,169 and U.S. Pat. No. 3,996,935. A number of skilled artisans have disclosed intraocular lens structures comprising an optical zone portion generally made of rigid materials such as glass or plastics suitable for optical use.

However, one of the principle disadvantages of the conventional rigid intraocular lens is that implantation of the lens requires a relatively large incision in the ocular tissue. This type of surgical procedure leads to a relatively high complication rate, among other disadvantages. For instance, the serious dangers associated with implantation of a rigid lens structure include increased risks of infection, retinal detachment, laceration of the ocular tissues, particularly with respect to the pupil, and displacement of the lens within the eye.

In addition, the principal disadvantages of conventional fixation systems is that they typically require either the use of sutures for positioning the lens within the eye (usually by attachment to the iris), or the use of relatively stiff supporting haptic flanges to hold the lens in position without sutures. The manipulations required to fixate lenses using sutures or stiff haptics increase the surgical trauma to the eye. Further, post-operative displacement of the lens can occur with either of these conventional systems. For instance, sutures may erode or break and release the lens from its fixated position. The relatively stiff haptic components of conventional sutureless designs can damage the ocular tissues/supporting structures during intra-operative lens manipulation; post-operatively these stiff haptics may then slip through the damaged areas to allow the lens to move out of position.

Recognizing these disadvantages, various artisans have attempted to overcome them. Flom (U.S. Pat. No. 3,991,426) and Hartstein (U.S. Pat. No. 4,262,370), for example, teach sutureless iris engagement fixation systems, and Anis (U.S. Pat. No. 4,251,887) and Simcoe teach sutureless fixation systems utilizing broadly curved flexible supporting loop haptics. Unfortunately, the iris engagements systems require relatively significant trauma to the iris with attendant post-operative complications. The latter known systems, while achieving fixation with little or no trauma to the iris, can still become displaced through relatively small tears in the capsular bag when they are positioned there. These tears are not uncommon, and may occur during the removal of the cataract or during the insertion of the lens.

Moreover, the bipodal design of the Simcoe lens reduces the planar stability of the lens within the eye, and the open loop configuration allows the lens to decenter if the eye heals unevenly or the lower supporting loop is flexed to the point of crimping during placement within the eye.

Accordingly, those skilled in the art have recognized a significant need for a fixation system for intraocular lens structures which avoids the use of sutures, but which will maintain placement of the lens once positioned in the eye, thereby providing a safer and more convenient surgical procedure and a more comfortable fit for the eye. The present invention fulfills these needs.

SUMMARY OF THE INVENTION

This invention relates to an improved system for atraumatic fixation of intraocular lens structures, for instance, following cataract removal procedures. In more detail, the unique system comprises a deformable, compliant, peripheral support frame surrounding a concentrically disposed optical zone portion of the lens, the frame having a minimum diameter at least about 20% larger than the diameter of the optical zone portion.

Briefly, and in general terms, the unique resilient support frame may be integral with the optical zone portion, that is, take the form of a substantially continuous peripheral flange or may be non-integral wherein the optical zone portion is suspended by a plurality of compliant fibers or webbing from the support frame.

The optical zone portion of the lens in accordance with the present invention may be either rigid, such as those fabricated from conventional materials of polymethylmethacrylate, glass, or the like, or may be deformable such as the intraocular lens structures disclosed in applicant's co-pending U.S. patent application Ser. No. 346,105.

The optical zone portion may typically possess any appropriate optical characteristics, for instance, of the corrective type wherein the human crystalline lens is left intact or of the replacement type where the human crystalline lens is removed from the eye and replaced by an artificial lens implant.

In more detail, the unique fixation system comprises an appropriately configured and sized frame member which is placed in the anterior chamber angle of the eye, the area between the posterior side of the iris and the ciliary processes, or within the capsular bag of the eye following a cataract removal procedure, or across the vitreous face behind the ciliary processes.

In a presently preferred embodiment, the frame is configured and sized in such a manner that once in position within one of the foregoing locations, the ocular tissue in front and behind the frame prevents displacement in the anterior or posterior axis.

The peripheral support frame is fabricated from suitable biologically inert materials, such as polypropylene, nylon or silicone rubber. The suspension threads for the optical zone portion of the intraocular lens may typically be fabricated from selected biologically inert materials, such as polypropylene. Alternately, a sheet of relatively thin elastic material, such as a diaphragm of silicone rubber may be utilized to effect suspension of the optical zone portion from the supporting ring.

Accordingly, the unique fixation system for intraocular lens structures avoids iris engagement and the use of sutures which can lead to significant irritation of the ciliary body with attendant difficulty in surgical technique to minimize damage to the iris. However, the inventive fixation system will maintain placement of the lens once positioned in the eye, thereby providing a safer and more convenient surgical procedure and a more comfortable fit for the eye.

BRIEF DESCRIPTION OF THE DRAWINGS

FIG. 10 is a front elevational view of one embodied fixation system for intraocular lens structures similar to that shown in FIG. 2, and further including means for intraocular manipulation or fluid flow through the lens;

FIG. 11 is a side sectional view of the intraocular lens structure of FIG. 10;

FIG. 12 is a front elevational view of an alternative embodiment of the inventive lens fixation system comprising a non-circular peripheral support frame designed to allow fluid flow around the longer sides of the lens which may also provide an expansion area in the event the lens is positioned in a cavity that is smaller than the longer diameter of the support frame;

FIG. 13 is a cross-sectional view taken substantially along line 13—13 of FIG. 12;

FIG. 14 is a front elevational view of an alternative fixation system in accordance with the present invention using a scalloped peripheral support frame to allow fluid flow around the periphery of the lens;

FIG. 15 is a cross-sectional view of the inventive fixation system shown in FIG. 14 taken substantially along the line 15—15;

FIG. 16 is a front elevational view of yet another alternative embodiment utilizing a peripheral supporting frame which comprises compressible portions to permit the lens to be fixated in a cavity smaller than the overall diameter of the lens and supporting structure assembly;

FIG. 17 is a cross-sectional view of the inventive fixation system shown in FIG. 16 taken substantially along the line 17—17;

FIG. 18 is a front elevational view of another embodied fixation system in accordance with the present invention. The peripheral support frame comprising compressible sizing elements designed to appropriately integrate with the available space between the peripheral support frame of the lens and the supporting ocular tissue; and FIG. 19 is a cross-sectional view of the embodied fixation system shown in FIG. 18 taken substantially along the line 19—19.

DESCRIPTION OF THE PREFERRED EMBODIMENTS

The present invention provides an improved system for atraumatic fixation of intraocular lens structures which comprises a deformable, compliant, peripheral support frame and a concentrically disposed optical zone portion which is resiliently suspended therefrom. The minimum diameter of the support frame is at least about 20% larger than the diameter of the optic. The unique fixation system of the invention facilitates surgical placement of the intraocular lens structure in the eye without the requirement of sutures, and without engagement of the iris.

Accordingly, the inventive lens structures may be utilized for placement of the lens in the anterior chamber or posterior chamber of the eye without sutures, following, for instance, cataract extraction procedure. Thus, a safer, more convenient, and more comfortable surgical procedure is achieved with minimized displacement of the intraocular lens structures within the plane of the lens after implantation.

Figure 1:
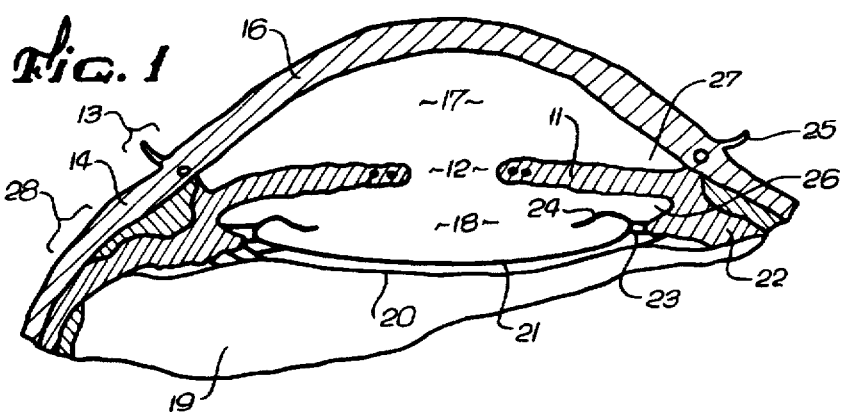
FIG. 1 is a partly side sectional view of a human eye for purposes of referencing the description of the unique fixation system for intraocular lens implants in accordance with the present invention, (the internal condition of the ocular area is that after extracapsular cataract extraction in accordance with conventional procedures)

Referring now to the drawing, denoted FIG. 1, there is shown a side cross-sectional view of the eye in stylized form illustrating the major ocular components: iris 11, pupil 12, limbus 13, sclera 14, after extracapsular cataract extraction in accordance with conventional procedure.

In more detail, FIG. 1 further depicts the cornea 16 composed of clear tissue which connects the sclera 14 at the limbus 13. The anterior segment of the eye is divided into two principle chambers by the iris 11 and pupil 12. The anterior chamber 17 is defined by the space between the cornea 16 and the iris 11. The posterior chamber 18 is defined in the space between the iris 11 and the vitreous 19.

In surgical procedures commonly known as intracapsular cataract extraction, the posterior chamber 18 is bounded by the hyaloid membrane 20. In surgical procedures commonly known as the extracapsular cataract extraction, the posterior chamber 18 is bounded by the posterior capsule 21 attached to the ciliary body 22 by means of zonular fibers 23. Portions of the anterior capsule may remain as flaps 24, creating with the posterior capsule 21, the ocular portion commonly known as the "capsular bag". The posterior chamber 18 peripheral area between the iris 11 and the extension of the ciliary body 22 is referred to as the ciliary sulcus 26. The anterior chamber peripheral area between the cornea 16 and the iris 11 is referred to as the angle 27 of the eye. The area of the sclera posterior to the plane of the iris and anterior to the vitreous 19 is known as pars plana 28.

With the foregoing referenced ocular components in mind, it is a principle feature of the present invention to provide fixation systems for various classes of intraocular lens structures, including those lenses with deformable optical zone portions and rigid optical zone portions such that the lens may be atraumatically placed within the eye without need for fixating sutures. Accordingly, the placement procedure minimizes the serious dangers associated with fixation by sutures; that is, increased risks of infection, and laceration of the ocular tissues, particularly with respect to the pupil.

Figure 2:
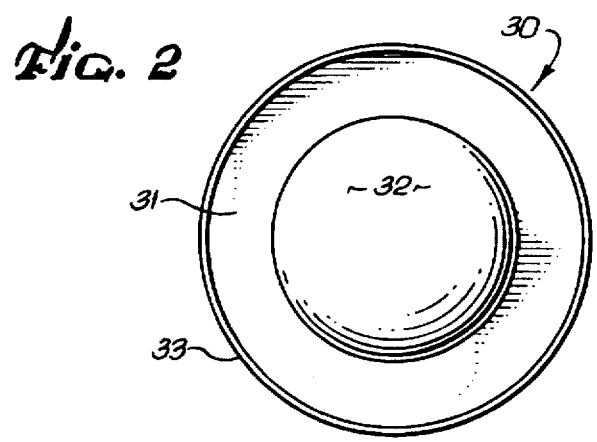
FIG. 2 is a front elevational view of one embodied fixation system for intraocular lens structures having a compressible peripheral support ring and a concentrically disposed optical zone portion in accordance with the present invention.

Referring now to the drawing, denoted FIG. 2, there is shown one embodied form of the improved fixation system for intraocular lens structures in accordance with the present invention. In this depicted embodiment, the fixation system (generally denoted 30) takes the form of a substantially continuous peripheral flange 31 surrounding a centrally disposed optical zone portion 32. This integral support ring or flange 31 may be appropriately configured and sized such that once positioned in the anterior chamber angle of the eye, the ciliary sulcus (the area between the posterior side of the iris and the ciliary processes), or within the capsular bag of the eye (following cataract extraction procedure). The ocular tissue in front of and behind the support frame 31 prevents displacement in the anterior or posterior axis.

More particularly, where the peripheral support frame is utilized for placement of the intraocular lens structure within the capsular bag, typical overall diameter of the support frame is from about 9 millimeters to about 12.5 millimeters. Where the peripheral support frame is sized to fit within the posterior chamber of the eye, behind the iris and in front of the ciliary processes, the typical overall diameter of the support frame would be within a range of from about 12.5 millimeters to about 14.5 millimeters. Further, where the peripheral support frame is to be utilized in placement of intraocular lens structures within the anterior chamber of the eye, the overall diameter of the support frame is typically from about 11 millimeters to about 14 millimeters.

Moreover, the flange or support frame is broadly curved, having a diameter at least about 20% greater than the diameter of the optical zone portion of the lens in all directions perpendicular to the optical axis. These broader curves help distribute the pressures imparted during intraocular manipulation of the lens while positioning it is place within the eye. Furthermore, they provide the implanted lens with a broader contact face to resist slippage through tears or holes within the supporting ocular tissue.

As will be readily appreciated by those skilled in the art, however, the foregoing typical dimensions are merely illustrative of a wide variety of suitable sizes included within the spirit and scope of this invention.

One important feature of the support frame, is that it possess the quality of being resiliently rigid but deformable and compliant possessing elasticity and desirable memory characteristics once imparted.

The foregoing characteristics facilitate placement of the lens assembly (support frame and optical zone portion) through a relatively small incision made in the ocular tissue or pupil which is relatively smaller than the overall diameter of the lens assembly by deformation, yet allow the support frame to return to its full size and configuration once placed in the eye. Moreover, these qualities make the lens assembly less susceptible to displacement should the lens assembly be subjected to a significant dislocating force.

In accordance with the present invention, the optical zone portion of the lens structure may generally be made of rigid materials, such as glass or plastic suitable for optical use, for example polymethylmethacrylate, but will preferably be deformable in accordance with my invention described in U.S. application Ser. No. 346,105, filed Feb. 5, 1982. In this latter respect, the optical zone portion of the intraocular lens will possess memory characteristics such that the lens can be deformed by compressing, rolling, folding, or stretching the optical zone portion to a diameter of 80% or less than the cross-sectional diameter of the optic during insertion into the eye, yet return to its original configuration, size and fixed focal length once imparted in the eye. Typically, the deformable optical zone portion is fabricated from one or more of suitable materials, such as polyurethane elastomer, silicone elastomer, hydrogel polymer, collagen compounds, organic or synthetic gel compounds and combinations thereof.

Those skilled in the art will readily appreciate that the optical zone portion of the lens in accordance with the present invention, can be fabricated having a base composed of any of the foregoing materials, and further comprise a surface layer or layers of a second and third material. Moreover, the lens may be tinted, colored or fabricated with occluded portions to yield desired transmission effects.

The intraocular lens structures in accordance with the present invention, can be fabricated having a wide variety of cross-sections designed for replacement of the surgically removed human crystalline lens or for refractive correction without removal of the human crystalline lens. In this respect, the optical zone portion may be a convex lens, a plano convex lens, a plano concave lens, a bi-concave lens, a concave-convex lens or have any other suitable cross-section.

Additionally, the intraocular lens structures in accordance with the present invention, may comprise means for assisting manipulation, placement, or fluid flow around or through the support frame of the lens. In this respect, the lens may be optionally provided with one or more holes, suitably located, which may extend entirely through the cross-section of the lens, or partly through the cross-section of the lens as an indentation or depression. Moreover, the peripheral support frame, for example, the peripheral flange or web connecting the optical zone portion to the peripheral support frame may be made of a gas or fluid permeable material.

Figure 3:
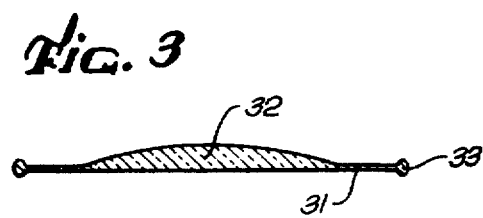
FIG. 3 is a side view of the fixation system and intraocular lens shown in FIG. 2.

FIG. 3 is a side view of the unique fixation system and intraocular lens shown in FIG. 2. As can be seen, the deformable support ring or flange 31 is integral with the optical zone portion 32. The end bead 33 of the flange 31 may, for instance, have a diameter of 0.25 millimeters, decreasing to a cross-sectional diameter of for instance, 0.01 to about 0.10 millimeters approaching the optical zone portion itself. The optical zone portion 32 will typically have a thickness of from about 0.05 millimeters to about 1.2 millimeters, depending upon refractive power, and a diameter in the range of from about 4 millimeters to about 6 millimeters. It is to be clearly understood however, that these dimensions are supplied as merely illustrative of one embodied form of the invention and not restrictive in terms of the dimensions nor configuration of the inventive system.

Figure 4:
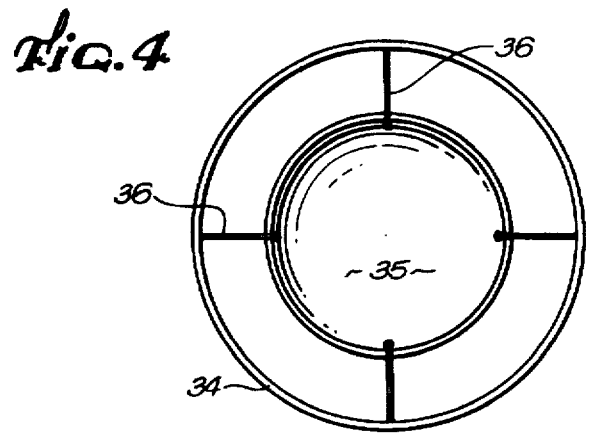
FIG. 4 is a front elevational view of a second embodied fixation system for intraocular lens structures, the optical portion being suspended by a plurality of threads or webbing from a non-integral peripheral support ring.

In a presently preferred embodiment of the invention, illustrated in FIG. 4, the fixation system comprises a non-integral peripheral supporting ring 34 and a concentrically disposed optical zone portion 35 which is suspended from the ring 34 in a floating fashion by a plurality of soft, compliant fibers or webbing 36. Peferably, the optical zone portion 35 is suspended from the ring by three or more threads 36 at suitable locations along the support ring 34.

As with the peripheral flange embodiment (FIGS. 2 and 3), the support ring 34 is resiliently rigid but compliant, to support the optical zone portion 35 of appropriate optical characteristics. In this respect, the peripheral ring 34 may be fabricated from a variety of suitable biologically inert and compatible materials such as polypropylene, nylon, stainless steel, silicone rubber, or the like. The threads or webbing may be fabricated from suitable biologically inert and compatible plastic material, such as polypropylene or, for instance, by a sheet of thin elastic material such as silicone rubber or the like.

Accordingly, the intraocular lens assembly will have the characteristics such that if the peripheral ring configuration is destroyed, no portion of the connecting suspensory system will support the weight of the optical zone portion. This feature allows the weight of the lens or other dislocating force, to be spread over a broad contact area, thereby minimizing trauma to the supporting ocular tissue. Further, as with the integral support ring, the non-integral support ring assembly may be modified from those embodiments shown to comprise holes, depressions or other grasping means to facilitate manipulation within the eye and to enhance fluid passage around the periphery of the lens.

Those readily skilled in the art will appreciate that while the figures herein depict support rings of substantially circular configuration, they may be widely modified in size and shape for placement within the eye.

One embodiment of the invention (depicted in FIG. 4) allows the peripheral support ring 34 to be retracted by the surgeon in a draw string manner to facilitate placement of the lens assembly through an opening (such as pupil or relatively small incision in the ocular tissue) which is smaller than the overall diameter of the intraocular lens assembly when the peripheral support ring is returned to its full size and original configuration once implanted in the eye.

Figure 5:
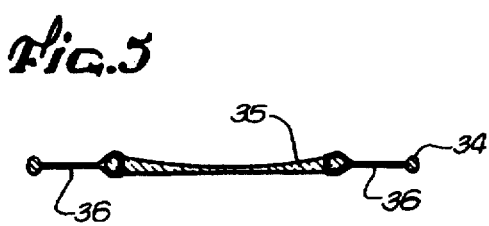
FIG. 5 is a side sectional view of the fixation system for intraocular lens structures depicted in FIG. 4.

FIG. 5 is a side sectional view of the intraocular lens assembly depicted in FIG. 4, the optical zone portion 35 being of the type for refractive correction of the human crystalline lens.

Figure 6:
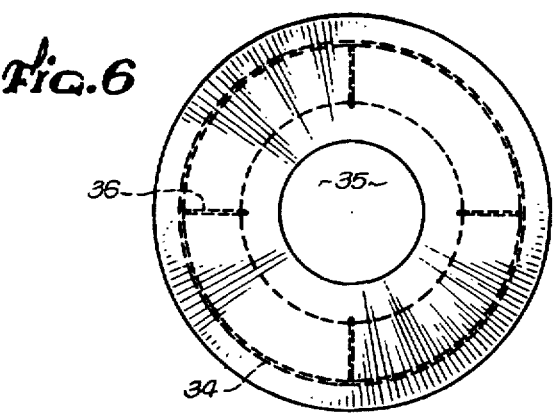
FIG. 6 is a front view illustrating the lens depicted in FIG. 4 fixated behind the iris and pupil of the eye.
Figure 7:
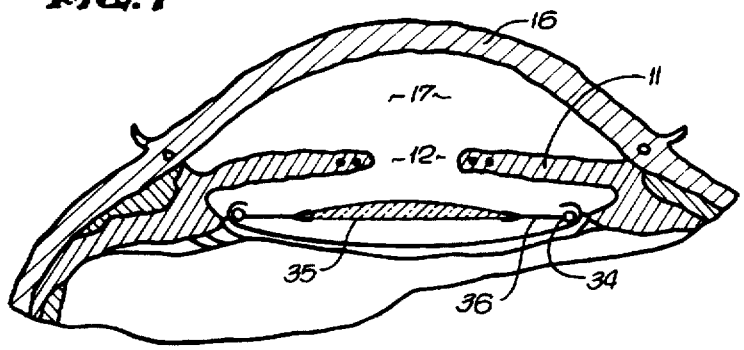
FIG. 7 is a side sectional view of the intraocular lens structure of FIG. 4 fixated in position within the capsular bag.

FIG. 6 is a front view of the intraocular lens assembly depicted in FIGS. 4 and 5, illustrating fixation of the lens behind the iris 11 and pupil 12 within the capsular bag. This embodied placement is seen most clearly in FIG. 7 of the drawings.

Accordingly, those skilled in the art will readily appreciate that the improved fixation system for intraocular lens structures in accordance with the present invention can be utilized to atraumatically fixate lens assemblies in the eye in a wide variety of locations and that the ocular tissue in front of and behind the peripheral support ring or flange will prevent displacement.

Figure 8:
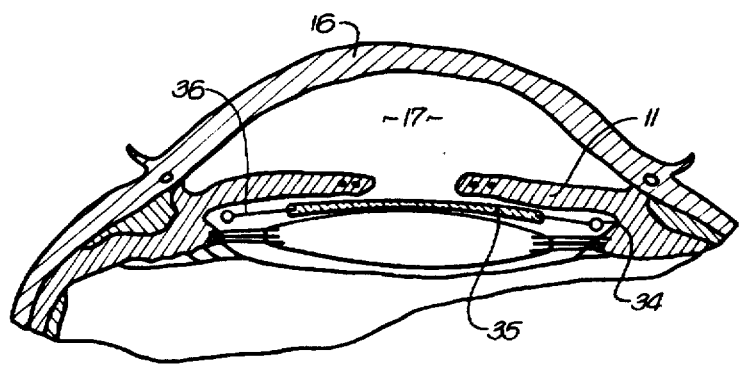
FIG. 8 is a side sectional view of an eye with natural crystalline lens intact and an intraocular lens of the corrective type as shown in FIG. 5 in position in the posterior chamber between the iris and the human crystalline lens.

FIG. 8 depicts the inventive intraocular lens assembly placed in the posterior chamber 18 of the eye, between the iris 11 and the human crystalline lens for refractive correction of the human crystalline lens without removal thereof.

Figure 9:
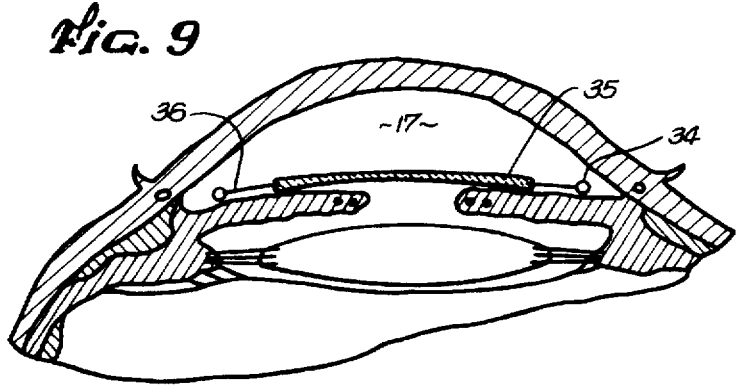
FIG. 9 is a cross-sectional view of an eye with human crystalline lens intact and an intraocular lens of the type shown in FIG. 5 in position in the anterior chamber of the eye for corrective purposes.

FIG. 9 illustrates an alternate positioning of the inventive intraocular lens assembly wherein the lens is positioned in the anterior chamber 17 of the eye with the natural crystalline lens still intact and in place.

FIG. 10 is a front elevational view of another embodied fixation system for intraocular lens structures in accordance with the present invention. The depicted lens structure is similar to that shown in FIG. 2, but includes means for intraocular manipulation 40 in the optical zone portion 32. The lens structure further comprises means for permitting fluid flow 41 through the lens.

As seen more clearly in FIG. 11, the depicted means for intraocular manipulation 40 may generally be described as a depression formed partly or completely through the cross-section of a portion of the lens. The means for assisting fluid flow through the lens 41 may generally be described as a hole fully extending through the cross-section of the lens. Of course, however, these features may be suitably located at other portions of the lens structure which will not interfere with the wearer's vision and comfort.

As shown in FIG. 12, an alternative embodiment of the lens fixation system comprises a non-circular peripheral support frame 42 surrounding an optical zone portion 43. The peripheral support frame 42 is of the form of a substantially continuous flange, previously described with reference to FIG. 3, but differs in configuration to allow fluid flow around the sides 44 and 45 of the lens. This configuration also provides an expansion area in the event the lens is positioned in a cavity that is smaller than the longer diameter of the support frame 42.

FIG. 13 is a cross-sectional view taken substantially along line 13—13 of FIG. 12 which further illustrates the embodied configured peripheral support frame.

FIG. 14 is a front elevational view of an alternative fixation system in accordance with the present invention comprising a scalloped peripheral support frame 46 and an optical zone portion 47. This configuration permits fluid flow around the periphery of the intraocular lens once implanted. A cross-sectional view of the embodied fixation system can be further seen in FIG. 15.

FIG. 16 illustrates yet another embodied fixation system in accordance with the present invention which comprises peripheral supporting frame 48 having compressible portions 49 and an optical zone portion 50. In this embodied form, the compressible portions 49 permit the lens to be fixated in a cavity smaller than the overall diameter of the lens and supporting structure assembly. The embodied lens is further shown in cross-section in FIG. 17.

FIG. 18 is a front elevational view of another embodied fixation system comprising a peripheral support frame 51 having compressible sizing elements 52 and an optical zone portion 53. The compressible sizing elements 52 enable the lens structure to appropriately integrate with the available space in the eye between the peripheral support frame 51 of the lens and the supporting ocular tissue. The embodied lens is further depicted in cross-section shown in FIG. 19.

In the foregoing embodied form, the compressible sizing elements 52 possess flexibility to take up space between the peripheral support ring and the supporting ocular tissue. This particular system utilizes open compressible loops spaced about the periphery of the supporting ring to allow the total lens assembly to be positioned and centered within any cavity that is larger than the peripheral support ring, but smaller than the overall diameter of total lens assembly including the cushioning structures.

Typically, the inventive intraocular lens structures in accordance with the present invention will have a total length of from about 9 millimeters to about 14 millimeters, a width of from about 4 millimeters to about 14 millimeters, and can be fabricated having a wide range of index of refraction. The optical zone portions will typically have a thickness of from about 0.1 millimeters to about 1.0 millimeters and a diameter in the range of from about 4 millimeters to about 6 millimeters.

Any conventional method for manufacture of the inventive lens assemblies can be utilized in accordance with the present invention to insure that the lens has the desired resiliency and compliancy. For instance, compression molding, transfer molding, injection molding, casting, machining, or a combination of these techniques may be utilized to produce the inventive lens assemblies.

Accordingly, the present invention offers a unique fixation system for intraocular lens structures after, for instance, cataract removal by way of small incision technique. The system therefore provides an implantation technique with attendant surgical safety convenience, and a comfortable fit for the eye.

The described intraocular lens assemblies thus minimize the principle disadvantages attendant with conventional fixation systems, that is, among other disadvantages, the serious dangers of increased risks of infection, retinal detachment, and laceration of the ocular tissues, particularly with respect to the pupil, and displacement of the lens from its proper position within the optic axis of the eye.

It will be apparent from the foregoing that, while particular forms of the invention have been illustrated and described, various modifications can be made without departing from the spirit and scope of the invention. Accordingly, it is not intended that the invention be limited, except as by the appended claims.

I claim:

1. An intraocular lens which comprises:

an optical zone portion;

a substantially resilient, deformable, compliant, annular skirt having a uniform surface continuous with the periphery of said optical zone portion of said lens structure;

said optical zone portion being deformable by compressing, rolling, folding, stretching or by a combination of such forces to temporarily reduce said optical zone portion to a diameter of 80% or less of the cross-sectional diameter of said optical zone portion in an unstressed state;

said annular skirt being integral with said optical zone portion and having a minimum diameter at least about 20% greater than the diameter of said optical zone portion in an unstressed state, in all directions perpendicular to the optical axis of said optical zone portion; wherein when placement is effected in the eye, the ocular tissue in front of and behind said annular skirt prevents displacement of the lens structure in the anterior or posterior axis without iris engagement.

2. The intraocular lens as defined in claim 1 wherein said optical zone portion is substantially rigid.

3. The intraocular lens as defined in claim 1 wherein said optical zone portion is deformable and possesses prescribed memory characteristics which enable the lens structure to be deformed by compressing, rolling, folding or stretching said optical zone portion to a diameter of 80% less of the cross-sectional diameter of said optical zone portion in an unstressed state, yet return to its original configuration, full size and fixed focal length after implantation in the eye.

4. The intraocular lens as defined in claim 1 wherein said annular skirt is configured and sized to fit within the capsular bag of the eye following cataract removal procedure.

5. The intraocular lens as defined in claim 1 wherein said annular skirt is configured and sized to fit within the posterior chamber of the eye, behind the iris and in front of the ciliary processes.

6. The intraocular lens as defined in claim 1 wherein said annular skirt is configured and sized to fit within the anterior chamber of the eye.

7. The intraocular lens as defined in claim 1 wherein said optical zone portion is composed of a polyurethane elastomer.

8. The intraocular lens as defined in claim 1 wherein said optical zone portion is composed of a silicone elastomer.

9. The intraocular lens as defined in claim 1 wherein said optical zone portion is composed of hydrogel polymer.

10. The intraocular lens as defined in claim 1 wherein said optical zone portion is composed of a collagen compound.

11. The intraocular lens as defined in claim 1 wherein said optical zone portion is composed of an organic gel compound.

12. The intraocular lens as defined in claim 1 wherein said optical zone portion is composed of a synthetic gel compound.

13. The intraocular lens as defined in claim 1 wherein said optical zone portion is composed of glass.

14. The intraocular lens as defined in claim 1 wherein said optical zone portion is composed of polymethylmethacrylate.

15. The intraocular lens as defined in claim 1 wherein said optical zone portion has a plano concave configuration.

* * * * *